United States Patent [19]

Elliott et al.

[11] Patent Number: 5,340,569
[45] Date of Patent: Aug. 23, 1994

[54] COLOR COSMETIC COMPOSITION

[75] Inventors: Marianne Elliott, Seymour; Lee A. Gallagher, Hamden; Caridad Hechavarria, New Haven, all of Conn.

[73] Assignee: Elizabeth Arden Co., Division of Conopco, Inc., New York, N.Y.

[21] Appl. No.: 943,164

[22] Filed: Sep. 10, 1992

[51] Int. Cl.⁵ .................. A61K 7/021; A61K 7/031
[52] U.S. Cl. ........................ 424/63; 424/69; 514/844
[58] Field of Search ............ 424/63, 401, 69

[56] References Cited

U.S. PATENT DOCUMENTS

| 4,272,514 | 6/1981 | Spence | 424/69 |
| 4,740,439 | 4/1988 | Tachikawa | 430/501 |
| 4,988,503 | 1/1991 | Macchio | 424/63 |
| 5,023,075 | 6/1991 | Macchio | 424/69 |
| 5,206,012 | 4/1993 | Farer | 424/69 |

FOREIGN PATENT DOCUMENTS 62-49247 10/1987 Japan.

Primary Examiner—Thurman K. Page
Assistant Examiner—Sally Gardner
Attorney, Agent, or Firm—Milton L. Honig

[57] ABSTRACT

A powdered molded color cosmetic composition, especially a blush formulation, is provided that includes an ultrafine boron nitride and a magnesium fatty acid salt, the combination being held in a pharmaceutically acceptable vehicle.

4 Claims, No Drawings

COLOR COSMETIC COMPOSITION

BACKGROUND OF THE INVENTION

1. Field of the Invention

The invention relates to a color cosmetic composition in powder form, especially for use as a blush formulation.

2. The Related Art

Molded powder color cosmetics in major part consist of fillers and extenders. Most often they are of the mineral variety. Illustrative are talc, kaolin, mica and silicon dioxide. In more limited amount, the extenders or fillers may be organic polymers including nylon and polyethylene. Often one or more of the aforementioned substances are blended together. These blends utilize relative proportions determined from consideration of skinfeel, spreadability, opacifying effect, moldability and adherence.

Boron nitride is a recent addition to the arsenal of useful extenders or fillers for press-molded color cosmetic compositions. For instance, Japanese Patent 62-49427 (Ohno et al) has reported that inclusion of boron nitride powder affords a product having good spreadability and adherence while being smooth, lustrous and of high covering power.

Investigations into the use of boron nitride powder has, however, revealed certain problems with skinfeel and moldability. Improvements would, therefore, be desirable in boron nitride containing systems.

Accordingly it is an object of the present invention to provide a pressed powder color cosmetic composition which exhibits improved properties of skinfeel, spreadability, creaminess, adhesion to skin and smoothness.

A further object of the present invention is to provide a pressed powder cosmetic color composition with good compression in manufacture.

A still further object of the present invention is to provide a pressed powder cosmetic color composition that is neither too dusty nor brittle.

These and other objects of the present invention will become more apparent by consideration of the following summary, detailed description and examples.

SUMMARY OF THE INVENTION

A powder color cosmetic composition is provided that includes:

(i) from about 0.001 to about 30% of an ultrafine powdered boron nitride;

(ii) from about 0.001 to about 30% of a magnesium $C_{12}$–$C_{20}$ fatty acid salt; and (iii) from about 0.5 to about 99% of a pharmaceutically acceptable vehicle.

DETAILED DESCRIPTION

Now it has been found that an improved pressed powder color cosmetic can be achieved that combines boron nitride with a magnesium $C_{12}$–$C_{20}$ fatty acid salt, the combination being delivered with a suitable powdered vehicle. Improved spreadability, adherence, skinfeel and covering power are achieved with this composition while still maintaining excellent manufacturing compressibility. Of particular improvement is the balance achieved between payoff (i.e. yield against brush stroke) and integrity of the pressed powder cake.

According to the present invention there is thus required as a first component an ultrafine powdered boron nitride. A wide variety of boron nitrides may be employed including the h-Bn, w-Bn, c-Bn, r-Bn and t-Bn varieties. Average particle size based upon spherical morphology can range from about 0.1 to about 30 microns, preferably from about 1 to about 10 microns, optimally between about 3 to about 7 microns. Most preferred is a boron nitride with a D50 mean value of 7.5 to 8 microns.

Amounts of the boron nitride powder may range from about 0.001 to about 30%, preferably from about 1 to about 10%, optimally from about 4 to about 7% by weight.

Another essential component of the present invention is that of a magnesium $C_{12}$–$C_{20}$ fatty acid salt. Most effective is magnesium myristate. Amounts of this component may range from about 0,001 to about 30%, preferably from about 0.5 to 10%, optimally from about 1 to 5% by weight. Average particle size (D50) for the magnesium fatty acid salt should range from about 5 to about 20, preferably from about 10 to about 15 microns.

A third element of the cosmetic composition according to the present invention is that of a pharmaceutically acceptable vehicle. The vehicle may be chosen from talc, inorganic pigments, metal oxide and hydroxides, mica, pearling pigments, organic pigments, mineral silicates, porous materials, carbons, metals, biopolymers and combinations thereof.

An important vehicle for use with compositions of the present invention is that of talc. The talc may have hydrophobic or hydrophilic surfaces, the former being achieved through treatment with a silicone such as a methicone. Amounts of the talc may range anywhere from about 1 to about 95%, preferably between about 30 and 70%, optimally between about 40 and 60% by weight. Talc average particle size should range from 0.5 to 9 microns, optimally between about 6 and 8 microns. Levels below 4 microns or above 9 microns are ordinarily unsatisfactory when combined with boron nitride powder.

Examples of inorganic pigments are ultramarine blue, Prussian blue, manganese violet and bismuth oxychloride.

Examples of metal oxides and hydroxides useful in the present invention are magnesium oxide, magnesium hydroxide, magnesium carbonate, calcium oxide, calcium hydroxides, aluminum oxide, aluminum hydroxide, silica, iron oxides ($a$-$Fe_2O_3$, $y$-$Fe_2O_3$, $Fe_3O_4$, FeO), iron hydroxides, titanium dioxide, titanium lower oxides, zirconium oxides, chromium oxides, chromium hydroxides, manganese oxides, cobalt oxides, nickel oxides and zinc oxides. These oxides and hydroxides may be used alone or in any mixture thereof. Furthermore, composite oxides and composite hydroxides such as iron titanate, cobalt titanate and cobalt aluminate can also be used in the present invention. Composite materials comprising metal oxides or hydroxides coated on the core materials (e.g. titanium oxides, coated mica, iron oxides coated nylon) also can be used in the present invention.

Examples of mica capable of being suitable for the present invention are muscovite, phlogopite, tiotite, sericite, lepidolite, paragonite and artificial or synthetic mica having a fluorine atom substituted for the hydroxyl group of natural mica as well as baked or calcined products thereof. These mica may be used alone or in any mixture thereof. Particularly preferred is a hydrophobic mica wherein the mineral has been coated with a silicone compound such as cyclomethicone or dimethicone.

Examples of organic pigments suitable for the present invention are C.I. 15850, C.I. 15850:1, C.I. 15585:1, C.I. 15630, C.I. 15880:1, C.I. 73360, C.I. 12085, C.I. 15865:2, C.I. 12075, C.I. 21110, C.I. 21095, and C.I. 11680, C.I. 74160 and zirconium, barium or aluminum lakes of C.I. 45430, C.I. 45410, C.I. 45100, C.I. 17200, C.I. 45380, C.I. 45190, C.I. 14700, C.I. 15510, C.I. 19140, C.I. 15985, C.I. 45350, C.I. 47005, C.I. 42053 and C.I. 42090.

The surfaces of these organic pigments may be treated with, for example, resins. These organic pigments may be used alone or in any mixture thereof.

Examples of pearling pigments (or nacreaous pigments) are bismuth oxychloride, guanine and titanium composite materials containing, as a titanium component, titanium dioxide, titanium lower oxides or titanium oxynitride. The titanium composite materials may be mixed with colored pigments such as iron oxides, Prussian blue, chromium oxide, carbon black and carmine. These pearling pigments may be used alone or in any mixture thereof.

Examples of mineral silicates suitable for the present invention are phyllosilicates and tectosilicates such as pyrophyllite, talc, chlorite, chrysotile, antigorite, lizardite, kaolinite, dickite, nacrite, halloysite, montmorillonite, nontronite, saponite, sauconite, and bentonite; natrolites such as natrolite, mesolite, scolecite, and thomsonite; heulandites such as heulandite, stilbite, epistibite; and zeolites such as analcite, harmotone, phillipsite, chabazite and gmelinite. These silicate minerals may be used alone or in combination thereof. The phyllosilicates may have organic cations at the interface of the layers thereof or may be substituted with alkali metal or alkaline earth metal ions. The tectosilicates may include metallic ions in the fine pores thereof.

Examples of porous materials suitable for the present invention are the above-mentioned silicate minerals; the above-mentioned mica; the above-mentioned metal oxides; $KAl_2(Al\ Si_3)O_{10}F_2$, $KMg(Al,\ Si_3)O_{10}F_2$, and $K(Mg,\ Fe_3)(Al,\ Si_3)O_{10}F_2$; carbonate minerals such as $CaCO_3$, $MgCO_3$, $FeCO_3$, $MNCO_3$, $ZnCO_3$, $CaMg(CO_3)_2$, $Cu(OH)_2CO_3$, and $Cu_3(OH)_2(CO_3)_2$; sulfate minerals such as $BASO_4$, $PbSO_4$, $CaSO_4$, $CaSO_4.2H_2O$, $CaSO_4.5(H_2O)$, $Cu_4SO_4(OH)_6$, $KAl_3(OH)_6(SO_4)_2$, and $KFe_3(OH)_6(SO_4)$; phosphate minerals such as $YPO_4$, $(CeLa)PO_4$, $Fe_3(PO_4)_2.8H_2O$, $Ca_5(PO_4)_3OH$ and $Ca_5(PO_4CO_3OH)_3F$, $OH)$; and metal nitrides such as titanium nitride and chromium nitride. These materials may be used alone or in any mixture thereof.

Examples of metals suitable for the present invention are iron, cobalt, nickel, copper, zinc, aluminum, chromium, titanium, zirconium, molybdenum, silver, indium, tin, antimony, tungsten, platinum and gold, and the alloys thereof.

Powdery biopolymer materials are also suitable for the present invention, especially by virtue of their high safety factor.

Examples of biopolymer materials suitable for the present invention are keratin (hair, fur, feather, down, horn, hoof, etc.), fibroin (silk), collagen (skin, hide, leather, tendon, bond, etc.), cellulose, hemicellulose, pectin, chitin, chondroitin, peptide-glucan, nucleic acid (DNA, RNA) and the like.

Any conventional cosmetic ingredients can be used together with the powder materials. Typical examples of such ingredients are various hydrocarbons such as squalane, liquid paraffin, and microcrystalline wax; emollient acids and alcohols such as caprylic acid, myristic acid, palmitic acid, stearic acid, oleic acid, isostearic acid, cetyl alcohol, hexadecyl alcohol and oleyl alcohol; emollient esters such as caprylate esters, cetyl-2-ethylhexanoate, ethylhexyl palmitate, 2-octyldodecyl myristate, 2-octyldodecyl gum ester, neopentyl glycol-2-ethylhexanoate, isooctyl triglyceride, 2-octyldodecyl oleate, isopropyl myristate, isostearic acid triglycerides, coconut oil fatty acid triglyceride, olive oil, avocado oil, beeswax, myristyl myristate, mink oil, lanolin and dimethyl polysiloxane; resins such as alkyd resins and urea resins; plasticizers such as camphor and acetyl tributyl citrate; UV absorbers; antioxidants; preservatives; surfactants; humectants; perfumes; water; alcohols and thickening agents.

Particularly preferred additional components are the volatile silicone oils represented by dimethicone and cyclomethicone. These may be present in amounts ranging from about 0.01 to about 10%, preferably between about 1 and about 5% by weight. Particularly preferred ester type ingredients are octyl palmitate and pentaerythritol tetra(2-ethyl hexanoate) and combinations thereof. The esters may be present in amounts from about 0.1 to about 20%, preferably between about 1 and 5% by weight.

Among the preservatives useful for the present invention are phenoxyethanol, ethyl paraben, isobutyl paraben, n-butyl paraben, methyl paraben, propyl paraben, sodium dehydroacetate and combinations thereof. The amount of preservative may range from about 0.01 to about 5%, preferably between about 0.10 and 2%, optimally between about 0.4 and 1% by weight.

Various herbal extracts may also be employed. Examples of these extracts are rosemary, althea, sambucus, matricaria and combinations thereof. Levels of the extract may range from 0.0001 to about 10%, preferably about 0.1 to about 2% by weight.

Compositions of the present invention advantageously will have all components of a similar average particle size, preferably between about 1 and about 8 microns, optimally between 2 and 7 microns. Uniformity of particle size may either be achieved by separately combining components of the proper size or by shear mixing the total composition down to the desired particle size range. A jet mill is particularly useful for purposes of shearing the total composition.

The following Examples will more fully illustrate the embodiments of the present invention. All parts, percentages and proportions referred to herein and in the appended claims are by weight unless otherwise indicated.

EXAMPLE 1

A blush formula according to the present invention which has been jet milled is outlined under Table I.

TABLE I

| Chemical or CTFA Name | Weight % |
| --- | --- |
| Talc BC | QS |
| Mica | QS |
| Mica & Silicon Dioxide | 4.00 |
| Bismuth Oxychloride | 2.00 |
| Magnesium Myristate | 2.00 |
| Boron nitride | 5.00 |
| Methyl paraben | 0.20 |
| Propyl paraben | 0.10 |
| Sodium Dehydroacetate | 0.20 |
| Dimethicone | 1.25–2.25 |
| Pentaerythritol tetra(2-ethyl hexanoate) | 1.25–2.25 |

TABLE I-continued

| Chemical or CTFA Name | Weight % |
| --- | --- |
| Octyl palmitate | 1.25-2.25 |
| Colorants | 8-10 |

Colorants listed below will vary in percentages due to shade. The colorant can range from 1 to 10% depending upon the shade. Total pigment level of blusher is approximately 8 to 10%.

| | |
| --- | --- |
| D&C Red 7 | C.I. 15850:1 |
| D&C Yellow 5 | C.I. 19140:1 |
| D&C Red 30 | C.I 73360 |
| D&C Red 6 | C.I. 15850 |
| D&C Orange 4 | C.I. 15510 |
| Carmine | C.I. 75470 |
| Chromium Oxide, Hydrous Green | C.I. 77289 |
| Chromium Oxide, Anhydrous Green | C.I. 77288 |
| Ultramarine Rose | C.I. 77007 |
| Brown Iron Oxide | C.I. 77491, 2, 9 |
| Red Iron Oxide | C.I. 77491 |
| Russet Iron Oxide | C.I. 77491 |
| Yellow Iron Oxide | C.I. 77492 |
| Black Iron Oxide | C.I. 77499 |
| Manganese Violet | C.I. 77742 |
| Ultramarine Blue | C.I. 7707 |
| Titanium Dioxide | C.I. 77891 |
| Prussian Blue | C.I. 77510 |
| Pearl Substrate: | |
| Mica and/or TiO$_2$; Carmine; | |
| Iron Oxides; Ferric Ferrocyanide; | |
| Ultramarine Rose; Manganese Violet; | |
| Chromium Oxide Hydrous/Anhydrous Green; | |
| Ferrocyanide; Bismuth Oxychloride. | |

EXAMPLE 2

A series of comparative experiments were conducted to evaluate the effects of certain metal fatty acid salts in conjunction with a boron nitride pressed powdered cosmetic. Table II sets forth the compositions of the test samples. The binder is a combination of octyl palmitate, pentaerythritol tetra(2-ethyl hexanoate) and dimethicone in approximately equal weight percent.

TABLE II

| | Sample (Wt. %) | | |
| --- | --- | --- | --- |
| Component | A | B | C |
| Talc J68 | 27.5 | 27.5 | 27.5 |
| Hydrophobic Mica | 27.5 | 27.5 | 27.5 |
| Boron Nitride | 20.0 | 20.0 | 20.0 |
| Binder | 3.0 | 3.0 | 3.0 |
| Red Iron Oxide (50%) | 2.0 | 2.0 | 2.0 |
| Zinc Stearate | 20.0 | — | — |
| Magnesium Stearate | — | 20.0 | — |
| Magnesium Myristate | — | — | 20.0 |
| | 100.0% | 100.0% | 100.0% |

Samples A, B and C were loaded into a press and compressed at 800 psi to a set fill line. Each of the resultant cakes had a weight of approximately 3 grams. These samples were then tested for hardness, for payoff and observed for surface properties when brushed.

TABLE III

| | Sample | | |
| --- | --- | --- | --- |
| Performance Properties | A | B | C |
| Penetrometer (mm) | 7.3 | 6.1 | 12.3 |
| Surface of Cake | Glazes | Glazes | No glazing |
| Payoff | Very little | Very little | Good |

Ordinarily, a blush-type color cosmetic should exhibit a penetrometer value between 7 and 15. Values less than 7 indicate an unacceptable brick-like cake. Values greater than 15 reflect cakes that are too soft and provide too much payoff when rubbed with a brush. Penetrometer readings listed in Table III are the average of three determinations with mean deviation ranging from 0.2 to 0.6.

Sample B with magnesium stearate exhibited a penetrometer reading of 6.1, a value indicating an unacceptable brick-like structure. Sample A formulated with zinc stearate fell just within the acceptable penetrometer values. However, it was observed that Samples A and B developed a glaze on the cake surface after being stroked by a brush 4 and 2 times, respectively. Payoff was also very poor. By contrast, Sample C exhibited an acceptable penetrometer value of 12.3 and glazing did not occur until after 20 strokes of a brush. Payoff was quite good with Sample C.

The foregoing description and examples illustrate selected embodiments of the present invention. In light thereof, various modifications will be suggested to one skilled in the art, all of which are within the spirit and purview of this invention.

We claim:

1. A powdered color cosmetic composition consisting essentially of:
   (i) from about 0.001 to about 30% of an ultrafine powdered boron nitride having an average particle size ranging from about 0.1 to about 30 microns;
   (ii) from about 0.001 to about 30% of magnesium myristate having an average particle size ranging from about 5 to about 20 microns; and
   (iii) from about 0.5 to about 99% of a pharmaceutically acceptable vehicle which is a talc having an average particle size of from 4 to 9 microns; and
   (iv) from 1 to 10% of a colorant selected from the group consisting of D&C Red 7; D&C Yellow 5; D&C Red 30; D&C Red 6; D&C Orange 4; Carmine; Green Chromium Oxide; Ultramarine Rose; Brown Iron Oxide; Red Iron Oxide; Russet Iron Oxide; Russet Iron Oxide; Yellow Iron Oxide; Black Iron Oxide; Manganese Violet, Ultramarine Blue, Prussian Blue; and combinations thereof.

2. A composition according to claim 1 wherein the talc has an average particle size ranging from 6 to 8 microns.

3. A composition according to claim 1 wherein the boron nitride has an average particle size ranging from 3 to 7 microns.

4. A composition according to claim 1 wherein the powdered color cosmetic is a blush formulation.

* * * * *